United States Patent [19]
Dunn et al.

[11] 3,981,297
[45] Sept. 21, 1976

[54] GAS SAMPLING CATHETER ASSEMBLY AND METHOD

[75] Inventors: Karl L. Dunn, Salt Lake City; Gordon S. Reynolds, Bountiful, both of Utah

[73] Assignee: Sorenson Research Co., Inc., Salt Lake City, Utah

[22] Filed: Mar. 3, 1975

[21] Appl. No.: 555,007

[52] U.S. Cl. .............................. 128/2 G; 128/2 E; 128/2 L; 128/214 R; 128/348
[51] Int. Cl.² ............................................ A61B 5/00
[58] Field of Search............ 128/2 E, 2 G, 2 L, 2 M, 128/2 R, 349, 348, 214 R, 214.4; 73/23 P, 1 R, 421.5 R

[56] References Cited
UNITED STATES PATENTS

| | | | |
|---|---|---|---|
| 3,224,433 | 12/1965 | Von Dalebor.......................... | 128/2 E |
| 3,572,315 | 3/1971 | Cullen.............................. | 128/349 R |
| 3,658,053 | 4/1972 | Fergusson et al.................... | 128/2 G |
| 3,824,157 | 7/1974 | Macur.............................. | 128/2 E X |
| 3,878,830 | 4/1975 | Bicher.............................. | 128/2 E |
| 3,893,448 | 7/1975 | Brantigan........................... | 128/2 G |

*Primary Examiner*—Kyle L. Howell
*Attorney, Agent, or Firm*—H. Ross Workman; J. Winslow Young

[57] ABSTRACT

A catheter assembly for sampling gases in biological tissue in vivo, including a catheter constructed of a hollow tube sheathed in a gas-permeable membrane, and an impermeable barrier between the tube and membrane to define the boundary of a sampling tip. A catheter hub slideably surmounts the catheter and detachably receives a calibration chamber normally surrounding the sampling tip. The method includes purging the calibration chamber with a calibration gas and thereafter removing the calibration chamber and inserting the catheter into the tissue to be sampled.

12 Claims, 17 Drawing Figures

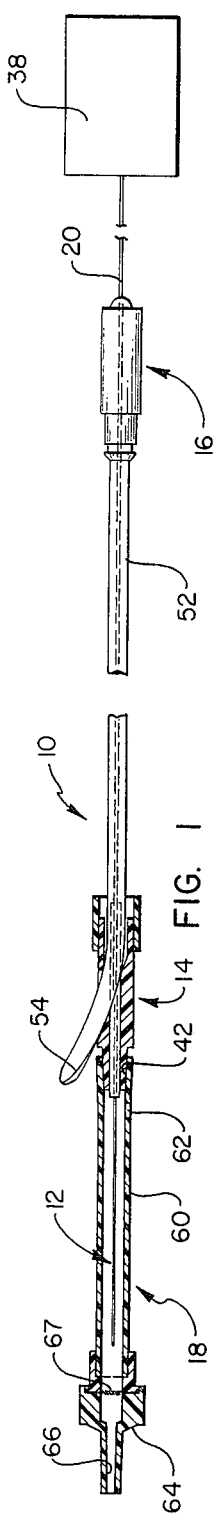
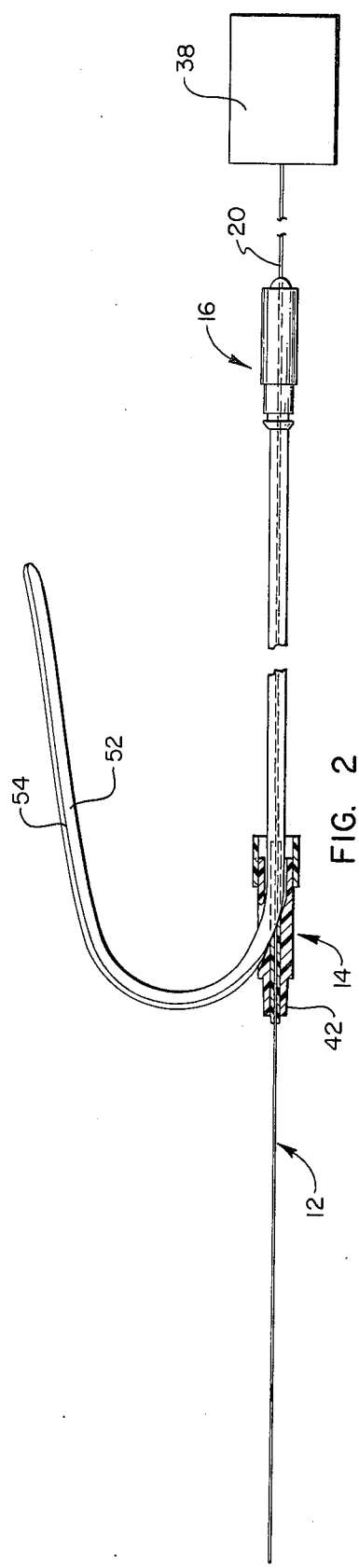
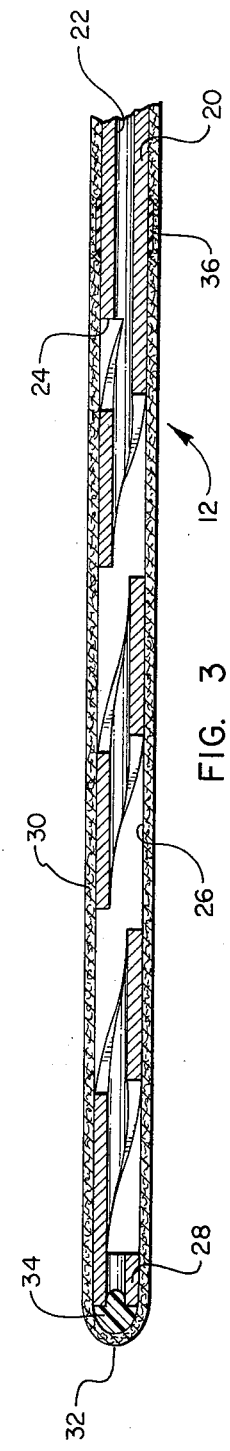

GAS SAMPLING CATHETER ASSEMBLY AND METHOD

BACKGROUND

1. Field of the Invention

The present invention relates to cannulae and more particularly to gas-sampling catheters and method for in vivo sampling of gases in biological tissue.

2. The Prior Art

The use of gas-sampling catheters is becoming increasingly more important as a diagnostic tool. Heretofore, gas determinations were made by analyzing a blood sample in vitro. More recently, catheters have been used to sample blood gases in vivo through an arterial or venous fistula.

Catheters for sampling gases in blood are well-known. See, for example, U.S. Pat. Nos. 3,572,315 and 3,658,053. Historically, however, the construction of conventional gas catheters has posed undesirable problems. Generally speaking, gas-sampling catheters of the prior art fall into two types. In the first type, a gas-permeable membrane is attached to a portion of the catheter while the remainder of the catheter comprises different material. This produces an undesirable joint presenting a potentially dangerous fragmentation site and adversely affects both gas sampling and sterility. Moreover, the joint tends to accelerate undesirable clot formation when the catheter is exposed to blood.

In the second type an unbroken membrane is provided over the entire length of the catheter. This type, however, has proved susceptible to inaccuracies as a result of the migration of gases between the membrane and the tube along the length of the catheter. For example, any portion of the catheter remaining outside of the patient's body during in vivo sampling would be adversely affected by atmospheric gases entering the membrane exterior of the puncture site.

The problems suggested above have proved even more acute when measuring gases in subcutaneous tissue other than blood. Further, until this present invention, liquids have been universally used to calibrate gas-sampling catheters. Liquids having known amounts of calibration gases are expensive and difficult to store. No catheter assembly or method has been heretofore devised to adequately calibrate the sampling portion of the catheter with readily obtainable gases.

It would, therefore, be a substantial improvement in the art to provide a gas-sampling catheter assembly and method overcoming the mentioned obstacles.

BRIEF SUMMARY AND OBJECTS OF THE INVENTION

The present invention includes an in vivo gas-sampling catheter having an unbroken exterior membrane for insertion into body tissues, the catheter having a sampling tip of predetermined size and structure which prevents undesirable migration of gases along the length of the catheter to the sampling tip. Further, structure and method are provided for calibrating the catheter by confining the sampling tip in a removable calibrating chamber prior to use.

It is, therefore, a primary object of the present invention to provide an improved catheter assembly.

It is another primary object of the present invention to provide an improved method for calibrating and sampling gases.

It is another object of the present invention to provide an in vivo gas-sampling catheter assembly having an unbroken exterior gas-permeable membrane along the entire insertable length of the catheter.

Another valuable object of the present invention is to provide a gas-impermeable barrier between the catheter tube and permeable membrane to inhibit axial migration of gases along the catheter to the sampling tip.

One still further object of the present invention is to provide improved structure accommodating calibration of the catheter at the sampling tip.

One further object of the present invention is to provide means for preserving the sterility of the catheter assembly.

These and other objects and features of the present invention will become more fully apparent from the following description and appended claims taken in conjunction with the accompanying drawings.

BRIEF DESCRIPTION OF THE DRAWING

FIG. 1 is an elevational view of a preferred catheter assembly embodiment shown partially in cross section.

FIG. 2 is an elevational view of the catheter assembly embodiment of FIG. 1 also shown in partial cross-section and illustrated with the membrane catheter in a partially advanced position.

FIG. 3 is a fragmentary cross-sectional view of a membrane catheter embodiment of the invention.

DETAILED DESCRIPTION OF THE PREFERRED EMBODIMENT

General

Figure 4:
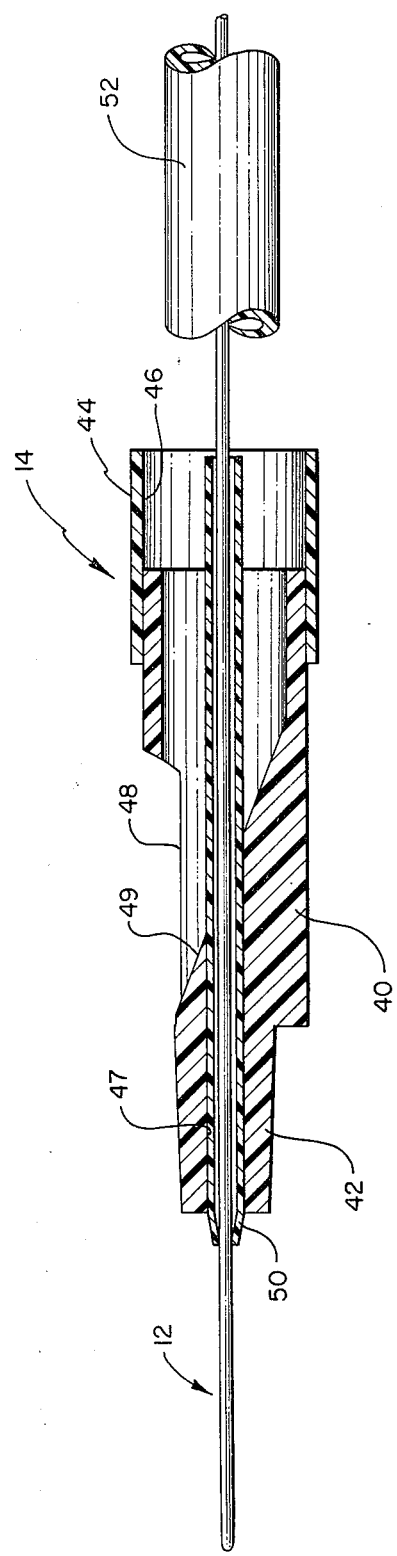
FIG. 4 is a fragmentary cross-sectional view of a catheter hub adapted to be used with the catheter of FIG. 3.
Figure 16:
FIGS. 5–16 are perspective elevations of various desirable catheter sampling tip embodiments.
Figure 15:
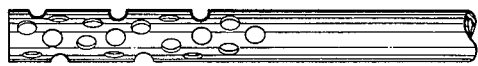
Figure 14:
Figure 13:
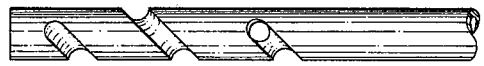
Figure 12:
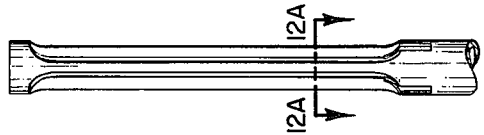
Figure 12A:
FIG. 12A is a cross-section taken along lines 12A—12A of FIG. 12.
Figure 11:
Figure 10:
Figure 9:
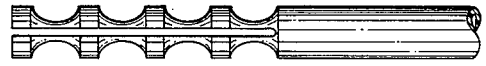
Figure 8:
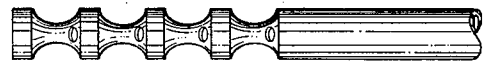
Figure 7:
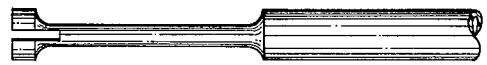
Figure 6:
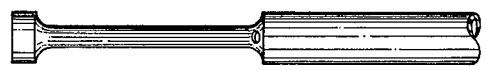
Figure 5:

It has been found according to the present invention that the catheter assembly described herein can be effectively used to sample biologically significant gases such as anesthesia, carbon dioxide and others both in vivo and in vitro. Of particular importance is the ability to aseptically deliver the gas-sampling catheter subcutaneously adjacent a particular muscle tissue site or directly intramuscularly to permit measurement immediately at the tissue site.

The Assembly

Reference is now made to the Figures wherein like parts are designated with like numerals throughout.

Referring now to FIG. 1, the catheter assembly generally designated 10 includes a catheter 12, a catheter hub 14, a base 16 and a calibration chamber 18 as will now be more fully described.

The catheter 12 can be best understood by reference to FIG. 3. The catheter 12 includes an elongated metal tube 20 having a hollow interior 22. The leading portion of the tube 20 has had a portion of its longitudinal length collapsed as at 24 and is thereafter twisted to form a spiralling core. This configuration presents a spirally configurated continuous opening 26 which communicates with the hollow 22 of the tube 20. Other suitable tip configurations are illustrated in FIGS. 5–16. The tube 22 terminates in a cylindrical collar 28.

Catheter 12 is covered with a gas-permeable membrane 30 along the entire length of the catheter from the collar 28 to the base 16 (FIG. 1). It has been found highly desirable to insure that the gas-permeable membrane traverses the entire length of the catheter without breaks or seams which tend to precipitate clot formation. In the presently preferred embodiment, it has been found that the catheter of the present invention can be used to measure tissue gases by inserting a substantial length of catheter (for example, 2 to 4 inches) directly into the tissue of a patient to sample gases therein. The continuous membrane 30 provides for facile insertion and minimizes contamination.

The tip 32 of the catheter 12 is rounded to facilitate insertion in biological tissue. In order to strengthen the tip 32 and prevent inadvertent fracture of the membrane 30, a bulbous insert 34 is attached adjacent the collar 28 and heat-sealed thereon to act as a forming mandrel and support for the tip 32. Preferably, the bulbous insert is formed of the same material as the membrane 30. While any suitable gas-permeable membrane material could be used, Teflon is presently preferred.

Elongated catheters of the type used in the prior art have been found to be adversely affected by ambient air. It has been found that even where the gas-permeable membrane is tightly adhered to the underlying tubing, gas tends to travel axially between the tube and the catheter. Thus, when a portion of the catheter is inserted into biological tissue for sampling purposes, the sample is distorted by ambient air travelling between the catheter and the tube. According to the present invention, the axial transference of gases is precluded by an annular barrier 36. The barrier is preferably made of gas-impermeable material such as epoxy and is heat-sealed directly to both the tube 20 and the gas-permeable membrane 30. Thus, the barrier 36 defines the trailing end of the sampling tip of the catheter 12.

The trailing end of the catheter 12 is rigidly anchored within the base 16. Preferably, the base 16 is formed of a gas-impermeable plastic material and the tube 20, absent the membrane 30, projects rearward of the base 16 to permit tight coupling into a receiver (not shown) of a conventional analyzer 38. The analyzer 38 can be of any suitable variety, one such analyzer being the Perkin & Elmer Mass Spectrometer.

The catheter 12 normally passes through the catheter hub 14, best shown in FIG. 4. The catheter hub 14 includes a body 40 having a forwardly tapered, diametrally reduced male coupling 42 forming the leading end of the hub 14. The trailing end of the hub is defined by a diametrally enlarged collar 44 mounted upon the body 40.

Interiorly, the hub 14 has a diametrally enlarged bore 46 which opens at the upper surface 48 of the hub for the reason to be made subsequently more apparent. A diametrally reduced bore 47 communicates coaxially with the bore 46 and opens to the exterior of the hub 14 at the leading end of the male coupling 42.

A tubular guide 50 is mounted in the bore 47 and projects into the bore 46 to the rear of the collar 44. Preferably, the guide 50 projects somewhat beyond the end of the male coupling 42. As shown in both FIGS. 1 and 4, the catheter 12 is telescopically disposed within the guide 50, the guide 50 at least at the leading tip being necked down and reduced thereby exerting a slight frictional force on the catheter. The guide 50 also prevents blood from moving through the hub 14 to contaminate the catheter 12.

Referring again to FIG. 1, the catheter is illustrated as enclosed within a conduit 52 which is provided with a longitudinal slit 54 along its entire length. The structure and operation of a suitable slit conduit can best be understood by reference to U.S. Pat. No. 3,185,152.

The conduit 52, which circumscribes the catheter 12 also surrounds a portion of the length of the guide 50 (FIG. 4) up to the ramp surface 49. The ramp surface 49 guides the conduit 52 out of the hub 14 and facilitates opening of the longitudinal slit 54 to separate the conduit from the catheter 12 without violating asepsis. Thus, when the catheter is advanced axially through the catheter hub from the FIG. 1 to the FIG. 2 position, the conduit 52 is automatically stripped away by the catheter hub.

Prior to use in sampling gases from biological tissue, the sampling tip of the catheter 12 is maintained within a calibration chamber 18 shown best in FIG. 1. The calibration chamber has a tubular body 60 preferably formed of plastic material and having an internal diameter sized so as to mate snuggly with the male coupling 42 of the catheter hub 14. The body 60 is provided with a discharge port 62 to permit the chamber 18 to be purged with calibration gas as will be hereinafter more fully described. The leading end of the calibration chamber 18 is mounted into a coupling 64 which defines an inlet port 66. In the illustrated embodiment, a filter 67 is located within the coupling 66 to remove contaminants from the calibrating gas. Preferably, the filter 67 is a bacterial filter to assure asepsis of the catheter 12 during calibration. While any suitable bacterial filter could be used, a 0.45 micron filter has been found acceptable. A filter (not shown) at the discharge port 62 may also be employed if desired.

Calibration gas is conducted through the inlet port 66 to purge the interior of the tube 60, the purged gases escaping at the discharge port 62. Because of the existence of the annular barrier 36 (FIG. 3) only the sampling tip need be supplied with calibrating gas, the remaining length of the catheter 12 being prevented from adversely affecting the sampled gas because of the barrier 36. The calibration chamber 18 may also be used for temperature stabilization of the catheter 12, when desired.

The Method

As has been heretofore pointed out, the catheter assembly of the present invention may be used to sample gases in blood, both in vivo and in vitro or, to sample gases subcutaneously adjacent selected tissues, such as muscle.

In using the catheter assembly described herein, it is observed that the sampling tip of the catheter 12 is aseptically preserved because of the sampling chamber 18. Prior to removing the sampling chamber 18, a calibration gas having a known concentration of the gas to be tested is conducted through the inlet port 66 to the interior of the tube 60. Asepsis is preserved through the filter 67. The tube 60 is purged through the discharge port 62. Thus, the analyzer 38 can be calibrated to the known gas composition. Oxygen, carbon dioxide, anesthesia, trace gases and the like can all be sampled when the analyzer 38 is calibrated to measure the gas.

Thereafter, the calibration chamber 18 is separated from the hub 14 and the catheter 12 is inserted through a previously made incision subcutaneously or intramuscularly adjacent the tissue to be sampled. Preferably, the catheter 12 is inserted from between 2 to 4 inches into the tissue to improve the reliability of the sample.

Alternatively, a fistula may be formed by cannulating an artery or other blood vessel in the manner taught in U.S. Pat. No. 3,459,183 and inserting the catheter 12 into the blood vessel through the fistula. It is pointed out that the coupling 42 is provided with a standard Luer taper to accommodate mating of the hub 40 with the trailing end of conventional cannulas. Blood is prevented from migrating along the catheter 12 by the reduced tip of guide 50, which acts as a check valve. Thus, contrary to the requirements of prior art devices, in vivo blood sampling can be accomplished without first sterlizing the patient's skin area at the sampling site.

As the catheter 12 is advanced into the tissue, the conduit 52 is automatically stripped away at the ramp surface 49 of the hub 14. The guide 50 exerts just enough tension on the catheter 12 to permit the catheter hub to be used to make the initial insertion and to properly guide the catheter 12.

The catheter assembly and method described herein have been found to obtain in vivo gas samples with surprising ease and facility. Moreover, the catheter may be used equally well to sample in vivo blood or tissue gases. Also, if desired, in vitro gases may be sampled because adverse interference with sampling is prevented even though the catheter is elongated because of the annular barrier 36.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A catheter for sampling gases in vivo comprising:
    a hollow generally flexible gas-impermeable tube having a leading end at least a portion of which is adapted to be inserted into the body of a patient;
    a gas-permeable membrane traversing the entire length of the insertable portion of the tube;
    means at the leading end of the tube for communicating the hollow of the tube and the inside of the gas-permeable membrane; and
    a gas-impervious barrier means circumscribing the tube between the tube and membrane behind the communicating means to prevent gas transfer to the leading end from membrane behind the barrier.

2. A catheter assembly for sampling gases in vivo comprising:
    a hollow gas-impermeable tube terminating in a tip insertable into the body of a patient;
    a gas-permeable membrane circumscribing the tip and the entire insertable portion of the tube;
    communication means associated with the insertable tip and providing communication between the inside of the insertable tip and the gas-permeable membrane;
    a gas-impervious barrier means interposed between the membrane and the tube adjacent the tip;
    a catheter hub, slideably surmounting the tube and membrane normally situated rearward of the tip, the hub comprising coupling means; and
    a diametrally enlarged calibration chamber removably mounted upon the coupling means and surrounding the catheter tip, the calibration chamber having a port for admitting calibration gases into the space around the catheter tip confined by the calibration chamber.

3. A catheter assembly as defined in claim 2 wherein said catheter hub comprises an interior guide through which the tube is axially displaced, the guide being diametrally reduced at the leading end of the hub to make friction contact with the membrane-covered tube.

4. A catheter assembly for sampling gases as defined in claim 2 further comprising an elongated conduit circumscribing that portion of the membrane-covered tube located rearward of the catheter hub, the conduit having a longitudinal slit which is automatically opened at the catheter hub to separate the membrane-covered tube from the conduit when the conduit is advanced through the hub.

5. A catheter assembly as defined in claim 2 further comprising a solid base rigidly mounted upon the hollow tube, the base revealing sufficient tube length to permit attachment to a conventional gas analyzer.

6. A catheter assembly as defined in claim 2 wherein said calibration chamber comprises a filter situated near the inlet port to filter calibration gases before the calibration gases reach the tip of the gas-permeable membrane.

7. A catheter assembly as defined in claim 2 wherein said calibration chamber comprises at least one discharge port to permit the interior of the calibration chamber to be purged with calibration gas.

8. A catheter assembly as defined in claim 2 wherein the communication means associated with the insertable tip of the gas impermeable tube comprises at least one surface interruption exposing the inside of the circumscribing membrane to the interior of the tube.

9. A catheter assembly for sampling gases comprising:
    an elongated tube comprising an exterior gas-permeable membrane, the leading end of the tube comprising a sampling tip;
    means communicating the inside of the sampling tip with the gas-permeable membrane;
    a calibration chamber having an internal diameter which is greater than the external diameter of the sampling tip, the calibration chamber removably surrounding the sampling tip; and
    means mounted upon the calibration chamber for communicating calibration gas to the interior of the calibration chamber thereby immersing the sampling tip in calibration gas having a known gas composition.

10. A catheter assembly as defined in claim 9 further comprising means mounted upon the calibration chamber for filtering contaminants from the calibration gas before the calibration gas reaches the sampling tip.

11. A method of sampling gases comprising the steps of:
    obtaining a gas sampling tube and covering the tube with a gas-permeable membrane, the tube having an opening at the tip thereof which opening is exposed to the membrane;
    providing a gas-impervious barrier between the tube and membrane near the tip of the tube so as to define a sampling tip of predetermined length;
    surrounding the sampling tip with a removable calibration chamber;
    admitting a predetermined gas into the calibration chamber around the sampling tip to accommodate calibration of the catheter prior to in vivo sampling; and thereafter situating the catheter adjacent tissue to be sampled.

12. A method of sampling gases as defined in claim 11 further comprising:

surrounding at least a portion of the length of the tube with a conduit, the conduit having a longitudinal slit therein; and slideably surmounting a hub upon the tube, the hub cooperating with the conduit to simultaneously open the conduit and separate the tube therefrom as the tube is advanced through the hub.

* * * * *